United States Patent [19]

Lavanish

[11] Patent Number: 4,507,145

[45] Date of Patent: * Mar. 26, 1985

[54] HERBICIDAL 3-[SUBSTITUTED 3- OR 5-ISOXAZOLYL]-1-4-, OR 5-SUBSTITUTED-2-IMIDAZOLIDINONES

[75] Inventor: Jerome M. Lavanish, Akron, Ohio

[73] Assignee: PPG Industries, Inc., Pittsburgh, Pa.

[ * ] Notice: The portion of the term of this patent subsequent to May 19, 1998 has been disclaimed.

[21] Appl. No.: 207,151

[22] Filed: Nov. 18, 1980

Related U.S. Application Data

[63] Continuation-in-part of Ser. No. 122,633, Feb. 19, 1980, Pat. No. 4,268,679.

[51] Int. Cl.³ ............... A01N 43/54; C07D 233/02
[52] U.S. Cl. .................................. 71/092; 548/247

[58] Field of Search ............... 548/247; 71/92

[56] References Cited

U.S. PATENT DOCUMENTS 3,544,582 12/1970 Albrect et al. .
3,773,780 11/1973 Metzger et al. .
3,847,935 11/1974 Moffett .
4,268,679 5/1981 Lavanish ................ 548/247

Primary Examiner—Anton H. Sutto
Attorney, Agent, or Firm—Edward J. Whitfield

[57] ABSTRACT

This invention concerns certain 3-[substituted 3- or 5-isoxazolyl]-1-4- or 5-substituted-2-imidazolidinones having herbicidal activity, their method of preparation, and the control of weeds therewith.

8 Claims, No Drawings

HERBICIDAL 3-[SUBSTITUTED 3- OR 5-ISOXAZOLYL]-1-4-, OR 5-SUBSTITUTED-2-IMIDAZOLIDINONES

CROSS-REFERENCE TO RELATED APPLICATIONS

This application is a continuation-in-part of copending, commonly assigned application Ser. No. 122,633 filed Feb. 19, 1980, now U.S. Pat. No. 4,268,679.

FIELD OF THE INVENTION

This invention concerns certain 3-[substituted 3- or 5-isoxazolyl]-1-4-, or 5-substituted-2-imidazolidinones having herbicidal activity, their method of preparation, and the control of weeds therewith.

DESCRIPTION OF THE INVENTION

This invention relates to 3-[3- or 5-substituted 3- or 5-isoxazolyl]-1-substituted-4-substituted, 5-substituted, or unsubstituted 2-imidazolidinones represented by the formula:

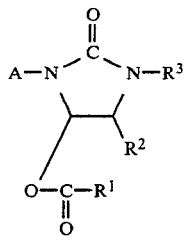

wherein:
A is

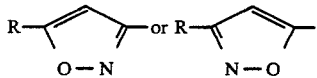

wherein R is alkyl or haloalkyl of up to 6 carbon atoms; cycloalkyl of from 3 to 8 carbon atoms; alkenyl or alkynyl of up to 5 carbon atoms; —$R^4$—O—$R^5$ or —$R^4$—S—$R^5$ wherein $R^4$ is alkylene of up to 6 carbon atoms and $R^5$ is alkyl of up to 6 carbon atoms; or

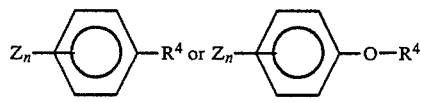

wherein Z is nitro, halogen, trifluoromethyl or $R^5$, and n is 0, 1, 2, or 3;

$R^1$ is alkyl or haloalkyl of up to 9 carbon atoms; cycloalkyl of from 3 to 8 carbon atoms; alkenyl or alkynyl of up to 5 carbon atoms, or

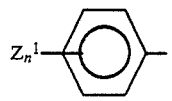

wherein $Z^1$ is nitro, halogen, trifluoromethyl, alkyl or alkoxy of up to 8 carbon atoms; and n is 0, 1, 2, or 3;

$R^2$ is hydrogen, hydroxy, alkyl of up to 4 carbon atoms, or allyl; and $R^3$ is alkyl of up to 3 carbon atoms or allyl.

Some alkyl groups of which the various constituents in the above formula are representative are, for example, methyl, ethyl, n-propyl, iso-propyl, n-butyl, iso-butyl, sec-butyl, pentyl, hexyl, heptyl, n-octyl, iso-octyl, nonyl, or the like, including combinations thereof, e.g. dimethylethyl. Exemplary alkoxy groups are methoxy, ethoxy, propoxy, butoxy, octoxy, and the like. As examples of cycloalkyl groups there may be mentioned cyclopropyl, cyclobutyl, cyclopentyl, cyclohexyl, cyclopentyl, and cyclooctyl. Allyl, butenyl, pentenyl, propynyl, butynyl, pentynyl and the like are exemplary of suitable alkenyl and alkynyl groups represented by the various constituents in the above formula. Representative suitable alkylene groups are, for example, methylene, ethylene, propylene, butylene, pentylene, or hexylene. As the halogen substituents, there may be mentioned chlorine, bromine, iodine, or fluorine, preferably chlorine or bromine.

Although any compound within the scope of the above formula is believed to have herbicidal activity in accordance with this invention, those compounds that have been found to be especially efficacious are 3-[5-(1,1-dimethylethyl)-3-isoxazolyl]-4-acetoxy-1-methyl-2-imidazolidinone, 3-[5-(1,1-dimethylethyl)-3-isoxazolyl]-4-benzoyloxy-1-methyl-2-imidazolidinone, and 3-[5-(1,1-dimethylethyl)-3-isoxazolyl]-4-butyryloxy-1-methyl-2-imidazolidinone.

The compounds of this invention may conveniently be prepared by reacting a 3-[5-substituted-3-isoxazolyl]-4-hydroxy-1-substituted-2-imidazolidinone of the formula:

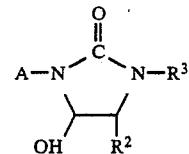

with an anhydride of the formula:

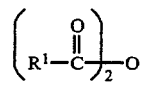

wherein A, R, $R^1$, $R^2$, $R^3$, X and Y are as previously defined. The above 3-[5-substituted-3-isoxazolyl]-4-hydroxy-1-substituted-2-imidazolidinones, which when reacted with the above anhydrides yield compounds of this invention, are described in copending, commonly assigned application Ser. No. 122,633 filed Feb. 19, 1980, of which application this application is a continuation-in-part. The anhydride may be obtained from commercial sources or prepared by known techniques.

More particularly, at least stoichiometric amounts of the reactants are reacted, preferably in the presence of an acid acceptor such as, for example, triethylamine, pyridine, N,N-dimethylaniline or the like, typically in the presence of an inert solvent such as, for example, benzene, methylene chloride, chloroform, ethyl acetate, tetrahydrofuran, or the like. The reaction mixture is typically heated to reflux and maintained at reflux until the reaction reaches the desired degree of completion.

The reaction mixture is then cooled to ambient temperature, washed, and allowed to phase separate. Product compound of the invention is recovered from the organic phase by any known technique, such as, for example, evaporation, crystallization, vacuum drying, or the like. If desired, the product may be further purified by, for example, recrystallization.

The following Examples are illustrative of the synthesis of certain specific compounds of this invention.

EXAMPLE I

Preparation of
3-[5-(1,1-dimethylethyl)-3-isoxazolyl]-4-acetoxy-1-methyl-2-imidazolidinone A 50-milliliter flask provided with a drying tube was charged with 1.0 gram of 3-[5-(1,1-dimethylethyl)-3-isoxazolyl]-4-hydroxy-1-methyl-2-imidazolidinone (prepared as described in Example 1 of U.S. application Ser. No. 122,633, filed Feb. 19, 1980), 0.5 gram of acetic anhydride, 0.5 gram of triethylamine and 20 milliliters of benzene. The flask contents were warmed slightly until the solution clarified. The reaction mixture was permitted to stand for about 20 hours after which the reaction mixture was transferred to a separatory funnel and washed consecutively with 50 milliliter aliquots of water, 5 percent aqueous hydrochloric acid solution, 5 percent aqueous bicarbonate solution and saturated brine. The organic phase was separated, dried over magnesium sulfate, filtered, and concentrated on a rotary evaporator at 55° C., yielding 1.2 grams of a pale yellow oil which was identified by mass spectrum analysis as 3-[5-(1,1-dimethylethyl)-3-isoxazolyl]-4-acetoxy-1-methyl-2-imidazolidinone.

EXAMPLE II

Preparation of
3-[5-(1,1-dimethylethyl)-2-isoxazolyl]-4-benzoyloxy-1-methyl-2-imidazolidinone A 50-milliliter flask provided with a reflux condenser, drying tube and magnetic stirring bar was charged with 1.0 grams 3-[5-(1,1-dimethyllethyl)-3-isoxazolyl]-4-hydroxy-1-methyl-2-imidazolidone (prepared as described in Example I of U.S. application Ser. No. 122,633, filed Feb. 19, 1980), 1.1 grams of benzoic anhydride, 0.5 gram of triethylamine and 20 milliliters of benzene. The flask contents were warmed slightly until the solution clarified and allowed to stand overnight with stirring. Thin layer chromatography indicated that the reaction was not complete and an additional 1.0 gram of benzoic anhydride and 0.5 gram of triethylamine were added. The reaction mixture was then heated to reflux and maintained at reflux for about 3.5 hours. After refluxing, the reaction mixture was permitted to stand at ambient temperature for 2.5 days. The reaction mixture was then transferred to a separatory funnel and washed consecutively with 50 milliliter aliquots of water, 5 percent aqueous hydrochloric acid solution, 5 percent aqueous sodium bicarbonate solution, 5 percent aqueous sodium bicarbonate solution, and saturated brine. The organic phase was separated, dried over magnesium sulfate, filtered, and concentrated on a rotary evaporator at 55° C., yielding 1.9 grams of a partially crystalline residue. The residue was recrystallized from a mixture of benzene and hexane yielding 0.8 gram of white crystals having a melting point of 165°–166° C. and identified by mass spectrum analysis as 3-[5-(1,1-dimethylethyl)-3-isoxazolyl]-4-benzoyloxy-1-methyl-2-imidazolidinone.

EXAMPLE III

Preparation of
3-[5-(1,1-dimethylethyl)-3-isoxazolyl]-4-butyryloxy-1-methyl-2-imidazolidinone A 50-milliliter flask provided with a reflux condenser and a magnetic stirring bar was charged with 1.0 gram of 3-[5-(1,1-dimethylethyl)-3-isoxazolyl]-4-hydroxy-1-methyl-2-imidazolidinone (prepared as described in Example I of U.S. application Ser. No. 122,633, filed Feb. 19, 1980), 1.3 grams of butyric anhydride, 0.8 gram of triethylamine and 10 milliliters of benzene. The reaction mixture was heated to reflux and maintained at reflux for about 3 hours after which the reaction mixture was cooled, transferred to a separatory funnel and washed consecutively with 50 milliliter aliquots of water, 5 percent aqueous hydrochloric acid solution, 5 percent aqueous sodium bicarbonate solution and saturated brine. The organic phase was separated, dried over magnesium sulfate, filtered, and concentrated on a rotary evaporator at 55° C., yielding 1.1 grams of an orange oil identified by mass spectrum analysis as 3-[5-(1,1-dimethylethyl)-3-isoxazolyl]-4-butyryloxy-1-methyl-2-imidazolidinone.

The mode of synthesis of specific compounds of this invention have been illustrated by the foregoing Examples; but it is to be understood that any compound contemplated within the scope of this invention may be prepared by those skilled in the art simply by varying the choice of starting materials and using the illustrated techniques or other suitable techniques.

The compounds of this invention are believed effective in regulating the growth of a variety of undesirable plants, i.e. weeds, when applied, in an herbicidally effective amount, to the growth medium prior to emergence of the weeds or to the weeds subsequent to emergence from the growth medium. The term "herbicidally effective amount" is that amount of compound or mixture of compounds required to so injure or damage weeds such that the weeds are incapable of recovering following application. The quantity of a particular compound or mixture of compounds applied in order to exhibit a satisfactory herbicidal effect may vary over a wide range and depends on a variety of factors such as, for example, hardiness of a particular weed species, extent of weed infestation, climatic conditions, soil conditions, method of application, and the like. Typically, as little as 0.2 or less pound per acre to 10 or more pounds per acre of compound or mixtures of compounds may be required. Of course, the efficacy of a particular compound against a particular weed species may readily be determined by relatively straightforward laboratory or field testing in a manner well known to the art.

The compounds of this invention may be used as such or in formulation with agronomically acceptable adjuvants, inert carriers, other herbicides, or other commonly used agricultural compounds, for example, pesticides, stabilizers, safeners, fertilizers, and the like. The compounds of this invention, whether or not in formulation with other agronomically acceptable materials, are typically applied in the form of dusts, granules, wettable powders, solutions, suspension, aerosols, emulsions, dispersions or the like in a manner well known to the art. When formulated with other typically used agronomically acceptable materials, the amount of compound or compounds of this invention present in the formulation may vary over a wider range, for example, from about 0.05 to about 95 percent by weight on weight of formulation. Typically such formulations will contain from about 5 to about 75 percent by weight of compound or compounds of this invention.

The compounds of this invention as exemplified by the compounds prepared in Examples I, II, and III have been found effective in controlling a variety of broadleaf and grassy weeds at application rates of as little as 0.25 pound per acre, preemergence or postemergence. The compounds prepared according to Examples I, II, and III were tested for herbicidal activity against various weed species under controlled laboratory conditions of light, temperature, and humidity, using techniques known to the art. In preemergence evaluation, a solvent solution of the test compound is applied at the desired rate to the weed species prior to emergence from the growth medium whereas in postemergent evaluation a solvent solution of the test compound is applied at the desired rate directly on the growing plant, the toxic effect of the compound being determined by visual inspection periodically after application.

Each of the compounds prepared in Examples I, II, and III were individually applied both preemergence and postemergence at application rates ranging from 0.25 to 1.0 pound per acre to broadleaf weeds, namely teaweed, jimsonweed, wild mustard, coffeeweed, velvetleaf, and morningglory and to grassy weeds, namely, yellow foxtail, crabgrass, johnsongrass, wild oats, and barnyardgrass. Within 21 days of application of each compound, each of the weed species was either killed or injured beyond recovery.

Although the invention has been described with specific references and specific details of embodiments thereof, it is to be understood that it is not intended to be so limited since changes and alterations therein may be made by those skilled in the art which are within the full intended scope of this invention as defined by the appended claims.

I claim:

1. A compound represented by the formula:

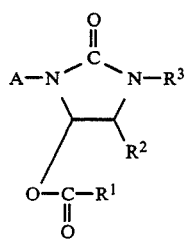

wherein:
A is

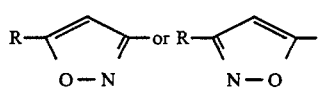

wherein R is alkyl or haloalkyl of up to 6 carbon atoms; cycloalkyl of from 3 to 8 carbon atoms; alkenyl or alkynyl of up to 5 carbon atoms; —$R^4$—O—$R^5$ or —$R^4$—S—$R^5$ wherein $R^4$ is alkylene of up to 6 carbon atoms and $R^5$ is alkyl of up to 6 carbon atoms; or

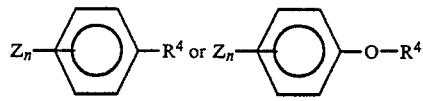

wherein Z is nitro, halogen, trifluoromethyl or $R^5$, and n is 0, 1, 2, or 3;

$R^1$ is alkyl or haloalkyl of up to 9 carbon atoms; cycloalkyl of from 3 to 8 carbon atoms; alkenyl or alkynyl of up to 5 carbon atoms, or

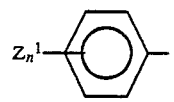

wherein $Z^1$ is nitro, halogen, trifluoromethyl, alkyl or alkoxy of up to 8 carbon atoms; and n is 0, 1, 2, or 3;

$R^2$ is hydrogen, hydroxy, alkyl of up to 4 carbon atoms, or allyl; and $R^3$ is alkyl of up to 3 carbon atoms or allyl.

2. The compound of claim 1 wherein R and $R^3$ are alkyl and $R^2$ is hydrogen.

3. A compound of claim 2 selected from 3-[5-(1,1-dimethylethyl)-3-isoxazolyl)]-4-acetoxy-1-methyl-2-imidazolidinone, 3-[5-(1,1-dimethylethyl)-4-benzoyloxy-1-ethyl-2-imidazolidinone, or 3-[5-(1,1-dimethylethyl)-3-isoxazolyl]-4-butyryloxy-1-methyl-2-imidazolidinone.

4. A herbicidal composition containing a herbicidally effective amount of a compound or mixture of compounds defined in claim 1.

5. In a method of controlling weed growth wherein a herbicidally effective amount of a herbicide is applied to growth medium prior to emergence of weeds from or applied to the weeds subsequent to emergence from the growth medium, wherein the improvement resides in using as the herbicide a herbicidally effective amount of a compound or mixture of compounds defined in claim 1.

6. A compound represented by the formula:

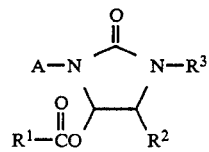

wherein
A is

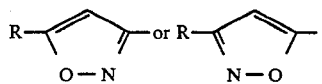

wherein R is hydrogen, alkyl or haloalky of up to 6 carbon atoms; cycloalkyl of from 3 to 8 carbon atoms; —$R^4$—O—$R^5$ or —$R^4$—S—$R^5$ wherein $R^4$ is alkylene of up to 6 carbon atoms and $R^5$ is alkyl of up to 6 carbon atoms;

$R^1$ is alkyl of up to 9 carbon atoms;

$R^2$ is hydrogen or alkyl of up to 4 carbon atoms; and
$R^3$ is alkyl of up to 3 carbon atoms.

7. In a method of controlling weed growth wherein a herbicidally effective amount of herbicide is applied to a growth medium prior to emergence of weeds therefrom or applied to the weeds subsequent to emergence from the growth medium, wherein the improvement resides in using as the herbicide a herbicidally effective amount of a compound or mixture of compounds defined in claim 6.

8. A herbicidal composition containing a herbicidally effective amount of a compound or mixture of compounds defined in claim 6.

* * * * *